US008711171B2

(12) United States Patent
Sano

(10) Patent No.: US 8,711,171 B2
(45) Date of Patent: Apr. 29, 2014

(54) IMAGE PROCESSING APPARATUS, METHOD, AND STORAGE MEDIUM FOR PERFORMING SOFT PROOF PROCESSING

(75) Inventor: Toshiyuki Sano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 455 days.

(21) Appl. No.: 13/176,647

(22) Filed: Jul. 5, 2011

(65) Prior Publication Data

US 2012/0032973 A1 Feb. 9, 2012

(30) Foreign Application Priority Data

Aug. 9, 2010 (JP) ................................ 2010-179004

(51) Int. Cl.
*G09G 5/02* (2006.01)
*H04N 1/60* (2006.01)
*G09G 5/06* (2006.01)

(52) U.S. Cl.
CPC .. *G09G 5/02* (2013.01); *G09G 5/06* (2013.01); *G09G 2320/0666* (2013.01); *H04N 1/6011* (2013.01)
USPC .......................................... 345/593; 345/589

(58) Field of Classification Search
CPC ... G09G 5/02; G09G 5/06; G09G 2320/0666; H04N 1/6011
USPC ................................................ 345/589, 593
See application file for complete search history.

(56) References Cited

U.S. PATENT DOCUMENTS

2004/0061700 A1 4/2004 Shioya .......................... 345/426
2011/0007333 A1* 1/2011 Ishii et al. ..................... 358/1.9

FOREIGN PATENT DOCUMENTS

JP 2004-126692 4/2004

* cited by examiner

*Primary Examiner* — Kee M Tung
*Assistant Examiner* — Ryan D McCulley
(74) *Attorney, Agent, or Firm* — Fitzpatrick, Cella, Harper & Scinto

(57) ABSTRACT

According to one aspect of the invention, an image processing apparatus includes: a lowpass filter generation unit configured to generate a lowpass filter corresponding to gonio-spectral reflection characteristics; a map generation unit configured to perform filter processing on intensity distribution of observation illumination in order to generate a map indicating a capture intensity distribution of observation illumination for a representative color; an intensity calculation unit configured to interpolate a capture intensity at a position corresponding to a pixel in the map in order to calculate a capture intensity of the observation illumination for the pixel; and a proofing color calculation unit configured to multiply the difference between a glossy component and a diffuse component by the capture intensity to calculate a proofing glossy component, and to add the diffuse component to the proofing glossy component in order to calculate a proofing color of the pixel.

9 Claims, 17 Drawing Sheets

FIG. 3

| RGB VALUE | INCIDENT ANGLE OF 45° ; EMERGENT ANGLE OF 0° (XYZ VALUE) | INCIDENT ANGLE OF 45°; EMERGENT ANGLE OF 1° (XYZ VALUE) | INCIDENT ANGLE OF 45°; EMERGENT ANGLE OF 2° (XYZ VALUE) | ... | INCIDENT ANGLE OF 45°; EMERGENT ANGLE OF 45° (XYZ VALUE) |
|---|---|---|---|---|---|
| (0, 0, 0) | (10, 10, 10) | (11, 11, 11) | (12, 12, 12) | ... | (55, 55, 55) |
| (0, 0, 16) | (20, 30, 40) | (22, 32, 42) | (24, 34, 44) | ... | (110, 120, 130) |
| ... | ... | ... | ... | ... | ... |
| (255, 255, 255) | (90, 100, 80) | (91, 101, 81) | (92, 102, 82) | ... | (135, 145, 125) |

| R | G | B | IMAGE CLARITY EVALUATION VALUE H |
|---|---|---|---|
| 0 | 0 | 0 | 45 |
| 0 | 0 | 32 | 38 |
| 0 | 0 | 64 | 39 |
| ⋮ | ⋮ | ⋮ | ⋮ |
| 255 | 255 | 255 | 60 |

FIG. 14A

| R | G | B | $X_{diff}$ | $Y_{diff}$ | $Z_{diff}$ |
|---|---|---|---|---|---|
| 0 | 0 | 0 | 7 | 8 | 6 |
| 0 | 0 | 32 | 8 | 9 | 9 |
| 0 | 0 | 64 | 9 | 9 | 11 |
| ⋮ | ⋮ | ⋮ | ⋮ | ⋮ | ⋮ |
| 255 | 255 | 255 | 209 | 235 | 233 |

FIG. 14B

| R | G | B | $X_{spec}$ | $Y_{spec}$ | $Z_{spec}$ |
|---|---|---|---|---|---|
| 0 | 0 | 0 | 190 | 215 | 220 |
| 0 | 0 | 32 | 178 | 200 | 170 |
| 0 | 0 | 64 | 177 | 199 | 158 |
| ⋮ | ⋮ | ⋮ | ⋮ | ⋮ | ⋮ |
| 255 | 255 | 255 | 275 | 318 | 195 |

FIG. 20

| K | R | G | B | x | y | LUMk (x, y) |
|---|---|---|---|---|---|---|
| 1 | 0 | 0 | 0 | 0 | 0 | 0 |
| | | | | 1 | 0 | 1 |
| | | | | ... | ... | ... |
| | | | | 255 | 255 | 10 |
| 2 | 0 | 0 | 64 | 0 | 0 | 0 |
| | | | | 1 | 0 | 0 |
| | | | | ... | ... | ... |
| | | | | 255 | 255 | 1 |
| ⋮ | ⋮ | ⋮ | ⋮ | ⋮ | ⋮ | ⋮ |
| n | 255 | 255 | 255 | 0 | 0 | 5 |
| | | | | 1 | 0 | 10 |
| | | | | ... | ... | ... |
| | | | | 255 | 255 | 14 |

IMAGE PROCESSING APPARATUS, METHOD, AND STORAGE MEDIUM FOR PERFORMING SOFT PROOF PROCESSING

BACKGROUND OF THE INVENTION

1. Field of the Invention

The present invention relates to an image processing apparatus and image processing method which perform soft proof processing of reproducing, on a monitor, a print product under observation illumination.

2. Description of the Related Art

Processing of using, for example, a PC (Personal Computer), to simulate the finish quality of an actual print product obtained by, for example, a printer, and displaying an image obtained by simulation is called soft proof processing. It is a common practice in soft proof processing to perform color matching processing for color components (to be referred to as diffuse components hereinafter) of light reflected by an actual print product, and faithfully reproduce their tonalities on a display device. In the recent soft proof processing, a technique of using CG (Computer Graphics) to simulate not only diffuse components of a print product but also glossy components (illumination reflection) of the print product is becoming prevalent.

To precisely reproduce (proof) glossy components of a target print product, it is necessary to reflect its gonio-spectral reflection characteristics on soft proof processing. The gonio-spectral reflection characteristics mean herein characteristics indicating the angle and intensity of reflection of light upon irradiation, and are referred to as a BRDF (Bidirection Reflectance Distribution Function). Especially in a pigment printer that has gained a large market share in recent years, the gonio-spectral reflection characteristics change for each color because the shape of the medium surface changes in accordance with, for example, the print density and the order of ink landing. Hence, it is necessary to precisely reflect the gonio-spectral reflection characteristics of each color on soft proof processing for a pigment printer.

Conventionally, in the CG field, the glossy components are represented using, for example, a Phong model obtained by approximating the gonio-spectral reflection characteristics. Also, to more accurately reflect the gonio-spectral reflection characteristics, a technique of combining a plurality of CG models to approximate the gonio-spectral reflection characteristics of the target has also been proposed (see, for example, Japanese Patent Laid-Open No. 2004-126692).

The CG model that is conventionally introduced to represent the glossy components generates an error with respect to actual gonio-spectral reflection characteristics. This makes it impossible to precisely represent the glossy components. Also, the technique of approximating a plurality of CG models to more accurately reflect the gonio-spectral reflection characteristics of the target can more accurately reflect specific gonio-spectral reflection characteristics on soft proof processing but nonetheless cannot cope with a situation in which the gonio-spectral reflection characteristics differ for each color.

SUMMARY OF THE INVENTION

The present invention has been made in order to solve the above-mentioned problems, and provides a technique of accurately reproducing glossy components of a print product subjected to observation illumination by precisely reflecting the gonio-spectral reflection characteristics of the print product, that differ for each color, on soft proof processing of reproducing the print product on a monitor.

According to one aspect of the invention, an image processing apparatus which performs soft proof processing of reproducing, on a monitor, a print product under observation illumination, comprises: a characteristics holding unit configured to hold, specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product; an evaluation value holding unit configured to hold, an evaluation value for each of the held color-specific gonio-spectral reflection characteristics; an intensity distribution holding unit configured to hold an intensity distribution of the observation illumination; a lowpass filter generation unit configured to obtain the gonio-spectral reflection characteristics for each of representative colors from the characteristics holding unit, and to generate a lowpass filter corresponding to the gonio-spectral reflection characteristics for each of the representative colors, where the representative colors corresponding to the evaluation values held in the evaluation value holding unit; a map generation unit configured to perform filter processing on the intensity distribution of the observation illumination held in the intensity distribution holding unit, for each of the representative colors, by means of the lowpass filter corresponding to the representative color, in order to generate a map indicating a capture intensity distribution of observation illumination for the representative color; an intensity calculation unit configured to obtain an evaluation value corresponding to a color of a pixel in a proofing-target image from the evaluation value holding unit, and to interpolate a capture intensity at a position corresponding to the pixel in the map for each of the representative colors, based on the evaluation value, in order to calculate a capture intensity of the observation illumination for the pixel, for each pixel in the proofing-target image; a proofing color calculation unit configured to obtain the glossy component and the diffuse component corresponding to a color of a pixel in the proofing-target image from the characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

According to another aspect of the invention, an image processing apparatus which generates a proofed image used to reproduce, on a monitor, a print product under observation illumination, comprises: a characteristics holding unit configured to hold, specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product; an evaluation value holding unit configured to hold, an evaluation value for each of the held color-specific gonio-spectral reflection characteristics; an intensity distribution holding unit configured to hold an intensity distribution of the observation illumination; a characteristics calculation unit configured to obtain the gonio-spectral reflection characteristics for each of representative colors from the gloss characteristics holding unit, and to calculate gonio-spectral reflection characteristics for a color of each pixel in the proofing-target image by means of obtaining the evaluation value corresponding to the color of the pixel from the evaluation value holding unit, and interpolating the gonio-spectral reflection characteristics for each of the representative colors, based on the evaluation value, where the representative colors corresponding to the evaluation values held in the evaluation value holding unit a lowpass filter generation unit configured to generate a lowpass filter corresponding to the gonio-spectral reflection characteristics for a color of each pixel in the proofing-target image; an intensity calculation unit configured to perform filter processing on the intensity distribution of the observation illumination held in the illumination intensity distribution holding unit, by means of the lowpass filter corresponding to a color of a pixel in the proofing-target image, in order to calculate a capture intensity distribution of the observation illumination for the pixel, for each pixel in the proofing-target image; a proofing color calculation unit configured to obtain the glossy component and the diffuse component corresponding to a color of a pixel in the proofing-target image from the characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

According to still another aspect of the invention, an image processing apparatus which generates a proofed image used to reproduce, on a monitor, a print product under observation illumination, comprises: a characteristics holding unit configured to hold, specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product; an intensity distribution holding unit configured to hold an intensity distribution of the observation illumination; a lowpass filter generation unit configured to obtain the gonio-spectral reflection characteristics for each of representative colors from the gloss characteristics holding unit, and to generate a lowpass filter corresponding to the gonio-spectral reflection characteristics, where the representative colors includes a plurality of colors in a color region of a proofing-target image; a map generation unit configured to perform filter processing on the intensity distribution of the observation illumination held in the intensity distribution holding unit by means of the lowpass filter, in order to generate a map indicating a capture intensity distribution of observation illumination for the representative color, and to generate a table indicating a relationship between the representative color and the map, for each of the representative colors; an intensity calculation unit configured to calculate a capture intensity of the observation illumination corresponding to a position and a color of a pixel in the proofing-target image by looking up the table, for each pixel in the proofing-target image; a proofing color calculation unit configured to obtain the glossy component and the diffuse component corresponding to a color of a pixel in the proofing-target image from the characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

According to yet another aspect of the invention, an image processing method is provided for an image processing apparatus comprising a characteristics holding unit, an evaluation value holding unit, a lowpass filter generation unit, a map generation unit, an intensity calculation unit, a proofing color calculation unit, and a display image generation unit, wherein the image processing apparatus performs soft proof processing of reproducing, on a monitor, a print product under observation illumination, wherein: the characteristics holding unit is configured to hold, specular reflection of the observation illumination as color-specific glossy components, diffuse reflection of the observation illumination as color-specific diffuse components, and color-specific gonio-spectral reflection characteristics; the evaluation value holding unit is configured to hold, an evaluation value for each of the held color-specific gonio-spectral reflection characteristics; and the intensity distribution holding unit is configured to hold an intensity distribution of the observation illumination; the method comprising: a lowpass filter generation step of obtaining the gonio-spectral reflection characteristics for each of representative colors from the characteristics holding unit, and generating a lowpass filter corresponding to the gonio-spectral reflection characteristics for each of the representative colors, where the representative colors corresponding to the evaluation values held in the evaluation value holding unit; a map generation step of performing filter processing on the intensity distribution of the observation illumination held in the intensity distribution holding unit, for each of the representative colors, by means of the lowpass filter corresponding to the representative color, in order to generate a map indicating a capture intensity distribution of observation illumination for the representative color; an intensity calculation step of obtaining an evaluation value corresponding to a color of a pixel in a proofing-target image from the evaluation value holding unit, and interpolating a capture intensity at a position corresponding to the pixel in the map for each of the representative colors, based on the evaluation value, in order to calculate a capture intensity of the observation illumination for the pixel, for each pixel in the proofing-target image; a proofing color calculation step of obtaining the glossy component and the diffuse component corresponding to a color of a pixel in the proofing-target image from the characteristics holding unit, multiplying the difference between the glossy component and the diffuse component by the capture intensity to calculate a proofing glossy component, and adding the diffuse component to the proofing glossy component in order to calculate a proofing color of the pixel, for each pixel in the proofing-target image; and a display image generation step of converting the proofing color into a signal value for the monitor to generate a display image, for each pixel in the proofing-target image.

The present invention enables accurately reproducing glossy components of a print product subjected to observation illumination by precisely reflecting the gonio-spectral reflection characteristics of the print product, that differ for each color, on soft proof processing of reproducing the print product on a monitor.

Further features of the present invention will become apparent from the following description of exemplary embodiments with reference to the attached drawings.

BRIEF DESCRIPTION OF THE DRAWINGS

FIG. 3 is a table showing the gonio-spectral reflection characteristics of each color of an actual print product in the first embodiment;

FIGS. 14A and 14B are tables illustrating examples of a diffusion LUT and a gloss LUT in the first embodiment;

FIG. 20 is a table illustrating an example of a representative color capture intensity map LUT in the third embodiment.

DESCRIPTION OF THE EMBODIMENTS

Embodiments of the present invention will be described in detail below with reference to the accompanying drawings. Note that the following embodiments do not limit the present invention defined by the scope of the claims, and not all combinations of features to be described in these embodiments are indispensable for the present invention.

First Embodiment

System Configuration

Figure 1:
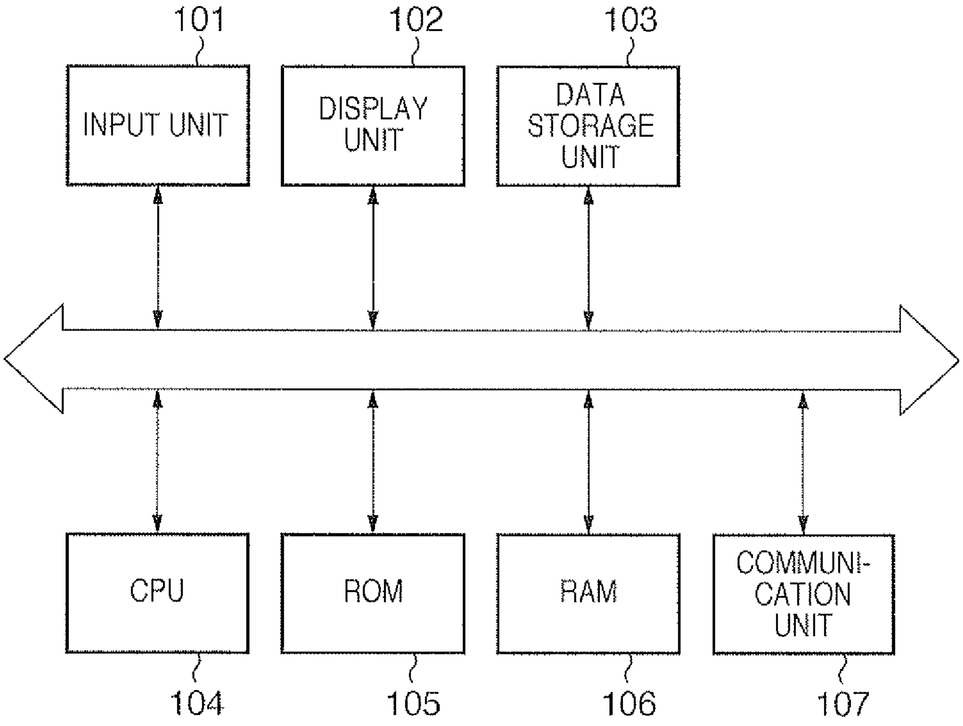
FIG. 1 is a block diagram showing the system configuration of an image processing apparatus in the first embodiment.

FIG. 1 shows the system configuration of an image processing apparatus which performs soft proof processing in the first embodiment. Referring to FIG. 1, an input unit 101 is a device which inputs data and an instruction from the user, and includes a keyboard and a pointing system such as a mouse. A display unit 102 is a display device (monitor) which displays, for example, a GUI, and uses, for example, a CRT or a liquid crystal display. A data storage unit 103 is a device which stores image data and a program, and generally uses a hard disk. A CPU 104 controls all types of processing in the above-mentioned respective configurations. A ROM 105 and a RAM 106 provide the CPU 104 with, for example, a program, data, and the necessary working area for processing in the CPU 104. If a control program necessary for processing in the CPU 104 is stored in the data storage unit 103 or ROM 105, it is executed upon being read into the RAM 106. However, if a program is received by the apparatus via a communication unit 107, it is executed upon being recorded in the data storage unit 103 and then read into the RAM 106 or being directly read from the communication unit 107 into the RAM 106. The communication unit 107 is an interface (I/F) used for communication between individual devices, and can operate in accordance with a known communication scheme such as Ethernet®, USB, IEEE, or Bluetooth. Although the system configuration includes various constituent elements other than those described above, a description thereof is not a principal part of the present invention and therefore will not be given.

Overview of Image Processing

Figure 2:
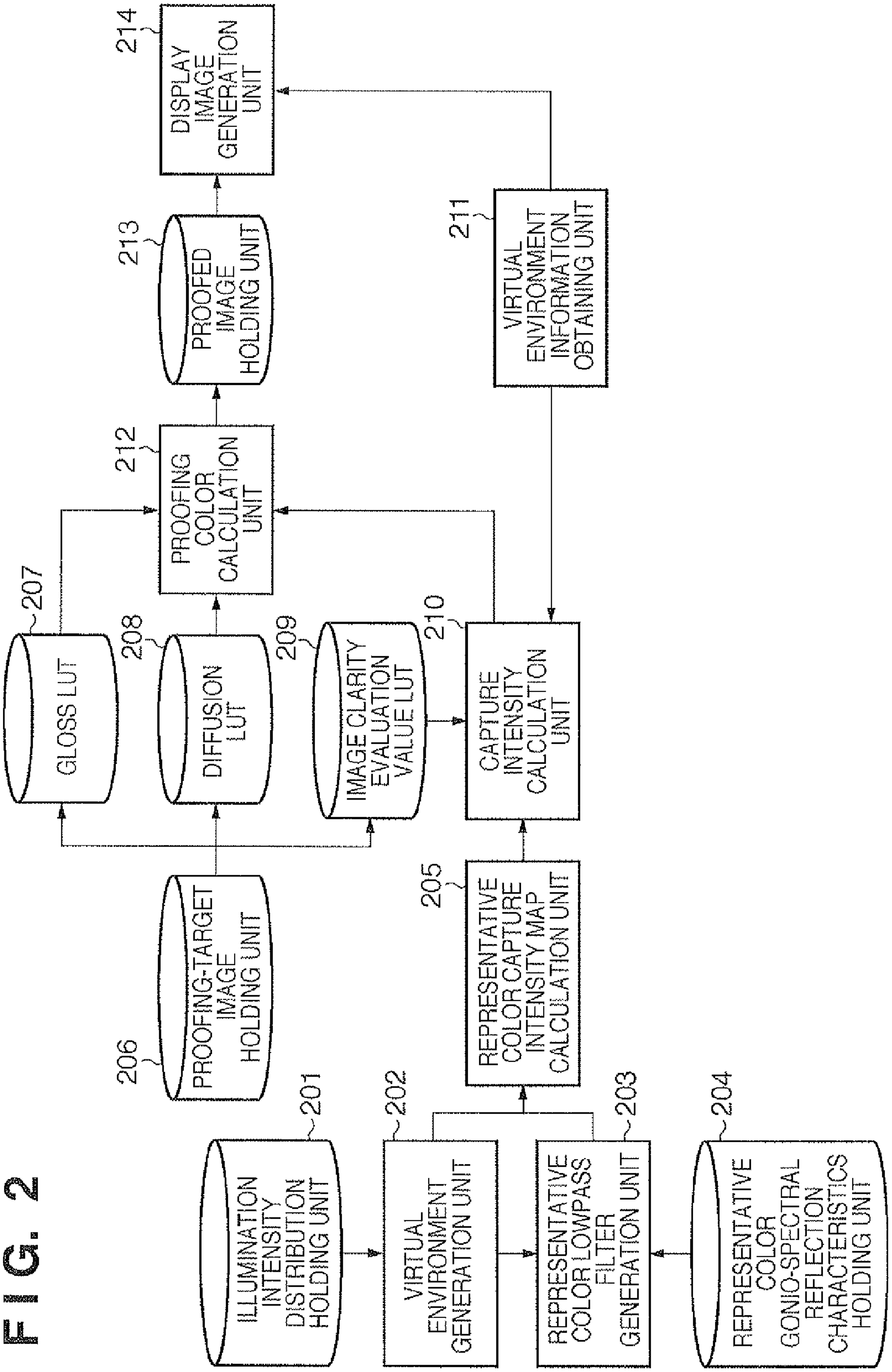
FIG. 2 is a block diagram showing a functional configuration in the first embodiment.

FIG. 2 is a block diagram showing image processing executed by the image processing apparatus in the first embodiment and the flow of data, that is, a functional configuration in this embodiment. The image processing apparatus in this embodiment performs soft proof processing of accurately reproducing a print product of image data to be printed (proofing-target image) on a monitor so as to reproduce its diffuse components including glossy components.

In this embodiment, first, a virtual environment generation unit 202 obtains an intensity distribution of illumination (to be referred to as observation illumination hereinafter) used to observe a print product (to be referred to as a proofing-target print product hereinafter) of a proofing-target image from an illumination intensity distribution holding unit 201. An environment (to be referred to as a virtual environment hereinafter) used to virtually observe the print product is generated by CG based on the obtained intensity distribution and virtual environment information designated via the input unit 101 by the user.

A representative color lowpass filter generation unit 203 obtains gonio-spectral reflection characteristics for a representative print color (to be referred to as a representative color hereinafter), which are held in a representative color gonio-spectral reflection characteristics holding unit 204 in advance, and generates a lowpass filter based on the obtained gonio-spectral reflection characteristics. The gonio-spectral reflection characteristics (BRDF) of a representative color mean herein data (BRDF(θ)) obtained by measuring in advance the reflection intensity (X, Y, and Z values) of an actual print product upon light irradiation at each emergent angle (θ) for the RGB value of each representative color defined on the actual print product, as shown in FIG. 3. Note that two colors are used as representative colors in this embodiment.

Figure 4:
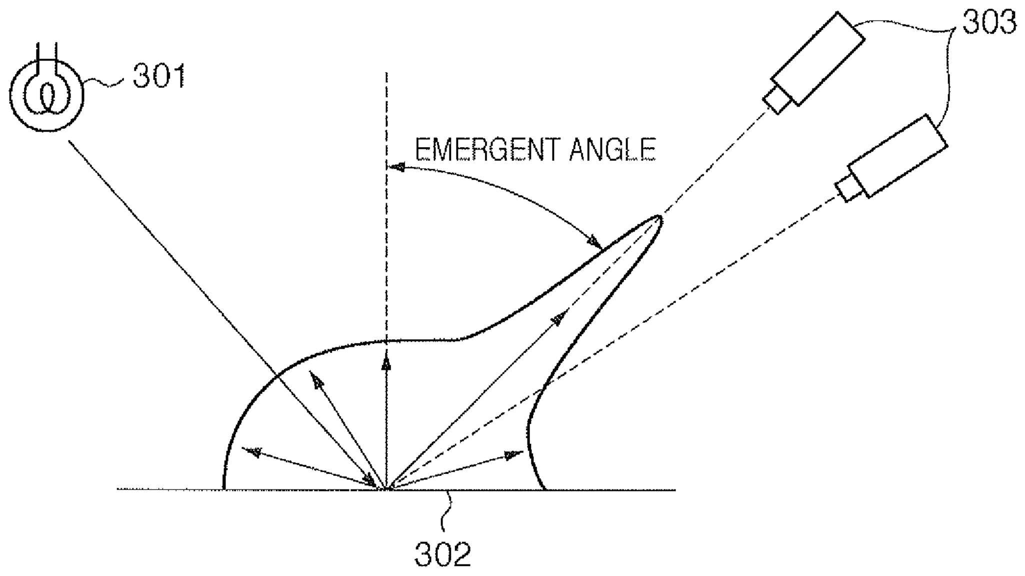
FIG. 4 is a view showing a method of obtaining the gonio-spectral reflection characteristics in the first embodiment.

FIG. 4 illustrates an example of a BRDF measurement method. Referring to FIG. 4, an actual print product 302 of a sample image having a plurality of color patches defined in the RGB space is irradiated with light using actual illumination 301, and light reflected at each emergent angle θ with respect to incident light is measured using a goniometer 303. The actual illumination 301 used to irradiate the actual print product 302 is not limited to a specific one as long as reflection characteristics for each angle on the actual print product 302 can be obtained.

Although gonio-spectral reflection characteristics BRDF are represented by X, Y, and values in this embodiment, as shown in FIG. 3, they may be represented using, for example, Lab values defined in an L*a*b* color space. Also, although gonio-spectral reflection characteristics BRDF(θ) corresponding to the emergent angle θ are measured upon fixing the incident angle at 45° in the example shown in FIG. 3, the measured value of gonio-spectral reflection characteristics BRDF when the incident angle is variable may be held in the representative color gonio-spectral reflection characteristics holding unit 204. Note that in the latter case, gonio-spectral reflection characteristics BRDF(θ) described by equation (2) (to be described later) use a bivariate function defined by the incident angle and the emergent angle.

A representative color capture intensity map calculation unit 205 performs filter processing, which uses the lowpass filter generated by the representative color lowpass filter generation unit 203, for the intensity distribution (observation illumination image) of observation illumination under the virtual environment generated by the virtual environment generation unit 202. With this filter processing, a representative color capture intensity map indicating the capture intensity of the observation illumination for the representative color of the proofing-target print product is calculated. The representative color capture intensity map is obtained by blurring the intensity distribution of the observation illumination in accordance with the gonio-spectral reflection characteristics of the representative color.

A virtual environment information obtaining unit 211 obtains specular reflection vector information in the virtual line-of-sight direction, which is calculated based on the virtual environment information input to the virtual environment generation unit 202. After that, a capture intensity calculation unit 210 calculates the capture intensity of the observation illumination for each pixel in the proofing-target image held in a proofing-target image holding unit 206. This calculation is done for each pixel in the proofing-target image using the representative color capture intensity map obtained by the representative color capture intensity map calculation unit 205, the specular reflection vector information obtained by the virtual environment information obtaining unit 211, and an image clarity evaluation value held for each color in an image clarity evaluation value LUT 209. The image clarity evaluation value means herein a value which has a high correlation with the gonio-spectral reflection characteristics BRDF held in the representative color gonio-spectral reflection characteristics holding unit 204, and is measured in advance for each color. In this embodiment, the full width at half maximum of the gonio-spectral reflection characteristics BRDF is held in advance in the image clarity evaluation value LUT 209 as an image clarity evaluation value indicating their variance.

A proofing color calculation unit 212 calculates a proofing color for each pixel in the proofing-target image. In this case, a proofing color is calculated using a glossy component and a diffuse component which are held for each color in a gloss LUT 207 and a diffusion LUT 208, respectively, and the capture intensity obtained by the capture intensity calculation unit 210.

In the above-mentioned way, when proofing colors for all pixels in the proofing-target image are calculated, they are converted into RGB values for monitor display and stored in a proofed image holding unit 213. Lastly, a display image generation unit 214 generates an image to be displayed on a monitor from the proofed image stored in the proofed image holding unit 213, in accordance with the vector information obtained by the virtual environment information obtaining unit 211, and a display instruction from the user. In this case, the monitor is the display unit 102.

Details of Image Processing

Figure 5:
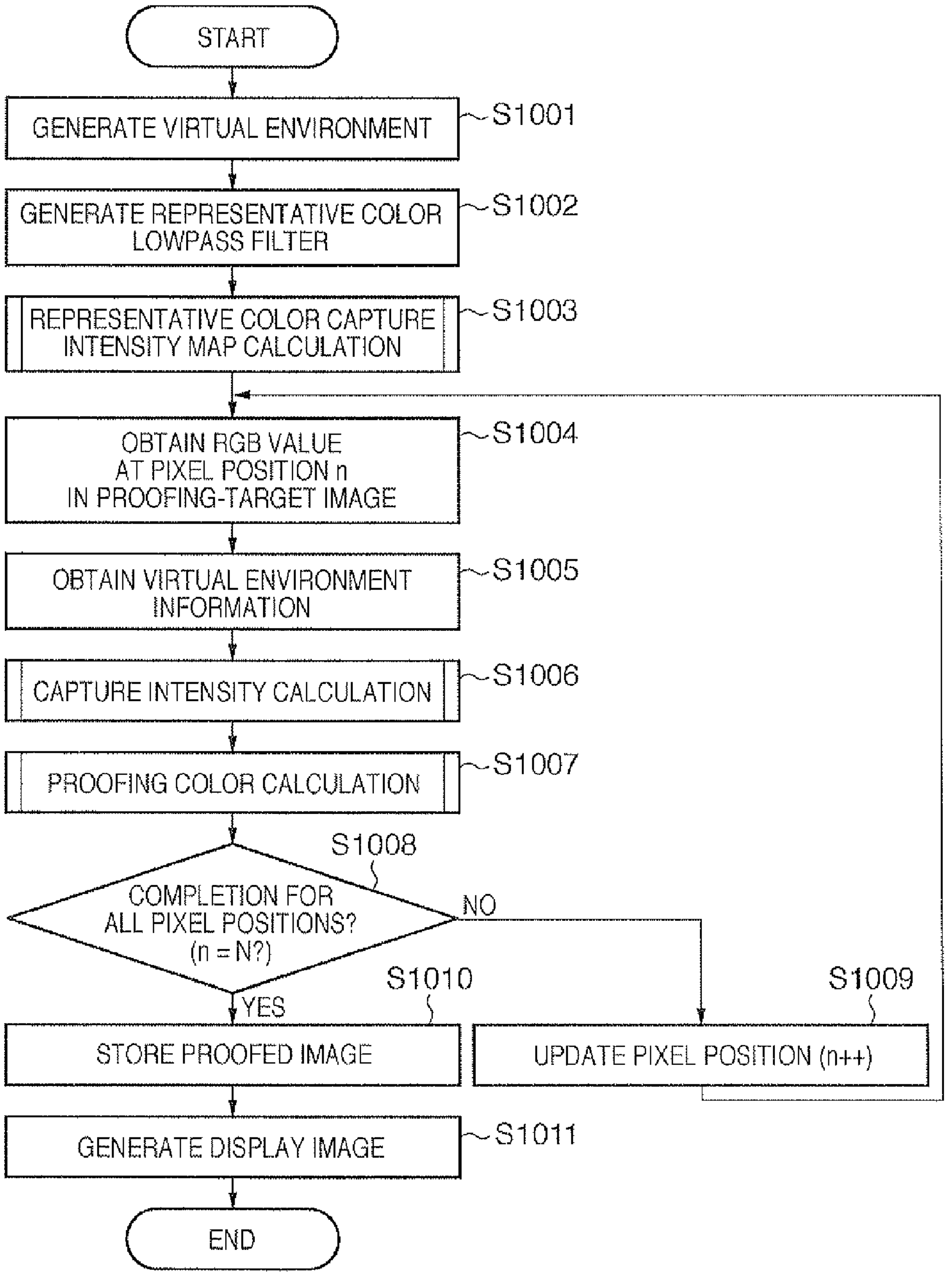
FIG. 5 is a flowchart showing image processing in the first embodiment.

Image processing in the first embodiment will be described in detail below with reference to a flowchart shown in FIG. 5. Note that the CPU 104 controls image processing in this embodiment, as described above.

Figure 6:
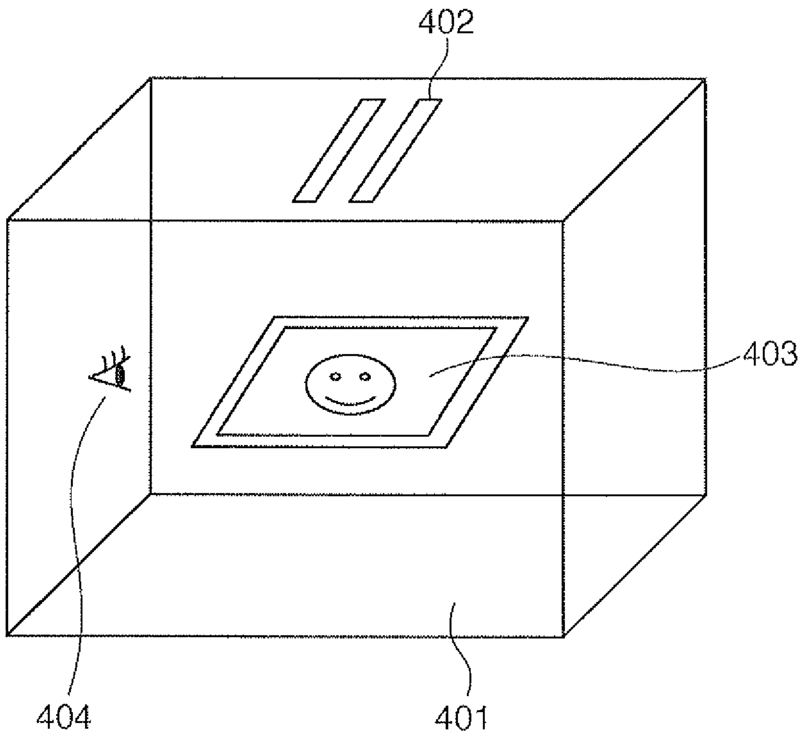
FIG. 6 is a view illustrating an example of a virtual environment in the first embodiment.

First, in step S1001, the virtual environment generation unit 202 generates an environment, used to virtually observe a print product, by means of CG based on virtual environment information designated via the input unit 101. More specifically, first, 3D objects such as a wall, a ceiling, and a floor, as shown in FIG. 6, are set to generate a virtual space 401. Next, virtual illumination 402 used to observe a virtual print product 403 is set, the virtual print product 403 is set near the center of the virtual space, and the position of a virtual point of sight 404 is set finally.

In this embodiment, an illumination intensity distribution obtained by, for example, a colorimeter for observation illumination under an environment (actual environment) used to actually observe a proofing-target print product is set as the virtual illumination 402. This illumination intensity distribution is data obtained by measuring the emission intensity of observation illumination on a two-dimensional plane (for example, the ceiling surface on which the virtual illumination 402 is set in the virtual space 401), and is held in the illumination intensity distribution holding unit 201 as two-dimensional data as shown in, for example, FIG. 7. Illumination intensity distribution data on a two-dimensional plane, which serves as the virtual illumination 402, will be referred to as an observation illumination image hereinafter. Although an example in which two-dimensional data (observation illumination image) on a given plane is used as an illumination intensity distribution will be given in this embodiment, the data form is not limited to a specific one as long as the position coordinates on the given plane and the illumination intensity can maintain a given relationship. Also, although an example in which an actually measured illumination intensity distribution is used has been given in order to more precisely proof glossy components, preset data held in advance in the CG model, for example, can also be used. Moreover, intensity distributions for a plurality of types of illumination may be held in the illumination intensity distribution holding unit 201, and an intensity distribution for observation illumination set as the virtual illumination 402 may be selectively used in this case.

In step S1002, the representative color lowpass filter generation unit 203 generates a lowpass filter for a representative color. More specifically, first, the gonio-spectral reflection characteristics BRDF(θ) of a representative color are read from the representative color gonio-spectral reflection characteristics holding unit 204. The representative color means herein two colors: a color which captures the observation illumination (gloss) the most clearly on the print product, and a color which captures the observation illumination the least clearly on the print product, that is, two colors having the maximum and minimum color-specific image clarity evaluation values, respectively, measured in advance. Next, a distance Dis [pixel] between the virtual illumination 402 and the virtual print product 403 under the virtual environment is obtained, and each emergent angle θ of the gonio-spectral reflection characteristics BRDF(θ) for each representative color is converted into a pixel count Pix indicating the distance from the irradiation point in BRDF measurement. This conversion is done in accordance with:

$$Pix = Dis \times \tan\theta \text{ for } 0° \le \theta \le 45° \quad (1)$$

Note that the θ range corresponds to the range of the emergent angle of the gonio-spectral reflection characteristics BRDF (θ), and is, for example, the range of 0° to 45° in the example shown in FIG. 3.

After that, based on the gonio-spectral reflection characteristics BRDF(Pix) for each pixel count Pix, a two-dimensional lowpass filter LPF(a,b) for each representative color is generated in accordance with:

$$LPF(a,b)=BRDF((a^2+b^2)^{1/2})$$

$$\text{for } -S\leq a\leq S,\ -S\leq b\leq S$$

$$S=\text{Dis}\times\tan 45°$$

$$(a^2+b^2)^{1/2}=S \text{ when } (a^2+b^2)^{1/2}\geq S \quad (2)$$

where a and b are coordinates indicating a position having, as its origin, the irradiation point on the virtual print product 403 in BRDF measurement, and S is a parameter indicating the filter size and corresponds to the value Pix at a maximum emergent angle (45°) in equation (1).

In step S1003, the representative color capture intensity map calculation unit 205 performs filter processing for each representative color for the observation illumination image formed by the virtual illumination 402, using the lowpass filter generated for each representative color in step S1002. Thus, a representative color capture intensity map is generated by blurring the luminance distribution of the virtual illumination 402 for each representative color in accordance with the gonio-spectral reflection characteristics of this representative color. Processing in step S1003 will be described in more detail later.

In step S1004, the proofing-target image holding unit 206 obtains the RGB value at a pixel position n in a proofing-target image. Note that the pixel position n is initialized (to, for example, 1) before processing in step S1004 for the first time. The RGB value at the pixel position n in the proofing-target image will simply be referred to as the RGB value hereinafter.

Figure 8:
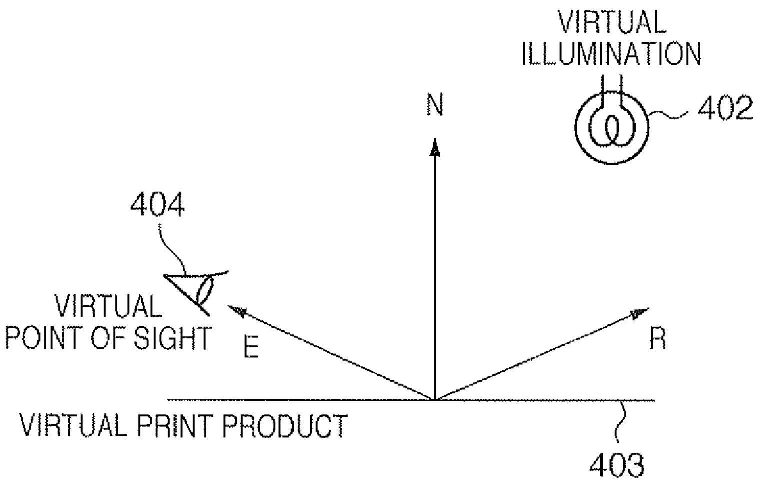
FIG. 8 is a view showing an overview of a reflection model under the virtual environment in the first embodiment.

In step S1005, first, the virtual environment information obtaining unit 211 obtains position information regarding the virtual print product 403 corresponding to the pixel position n in the proofing-target image, in accordance with the virtual environment information referred to in step S1001 as well. A specular reflection vector R for a line-of-sight vector E in the glossy reflection model shown in FIG. 8 is calculated for the obtained position. This calculation is done in accordance with a glossy component expression based on the glossy reflection model shown in FIG. 8 as given by:

$$R=-E+2(N\cdot E)N \quad (3)$$

As shown in FIG. 8, N is a vector indicating the normal direction to the surface of the virtual print product 403, and is obtained from the information of the virtual print product 403 designated by the user; E is a vector indicating the line-of-sight direction of the virtual point of sight 404 under the virtual environment; R is a vector indicating the specular reflection direction of the vector E; and (N·E) is the inner product of the vectors N and E.

In step S1006, the capture intensity calculation unit 210 calculates the capture intensity of the virtual illumination 402 at the pixel position n in the proofing-target image (that is, on the virtual print product 403). First, an image clarity evaluation value for the RGB value at the pixel position n is obtained from the image clarity evaluation value LUT 209. Note that the image clarity evaluation value means herein the full width at half maximum of the gonio-spectral reflection characteristics BRDF indicating their variance, as described above. The capture intensity of the virtual illumination 402 for the RGB value at the pixel position n is calculated using the obtained image clarity evaluation value and the representative color capture intensity map calculated in step S1003. Processing in step S1006 will be described in more detail later.

In step S1007, the proofing color calculation unit 212 calculates a proofing color for the pixel position n in the proofing-target image using the gloss LUT 207, the diffusion LUT 208, and the capture intensity calculated in step S1006. Processing in step S1007 will be described in more detail later.

In step S1008, it is determined whether proofing color calculation is complete upon processing in steps S1005 to S1007 for the total number of pixels N in the proofing-target image, that is, whether the pixel position n that is currently being processed in the proofing-target image. If n=N, the process advances to step S1010; or if n≠N, the process advances to step S1009, in which the pixel position n is incremented, and the process returns to step S1004.

In step S1010, the proofing color calculation unit 212 converts the proofing color calculated in step S1007 into a signal value for monitor display, and stores it in the proofed image holding unit 213 as a proofed image, for all pixels in the proofing-target image. In this case, the proofing color is converted into a signal value for monitor display by means of, for example, a conversion formula from an XYZ value ($X_{out}$, $Y_{out}$, $Z_{out}$) of the proofed image into an sRGB value ($R_{out}$, $G_{out}$, $B_{out}$) as presented in:

$$\begin{pmatrix} R_{out\_Linear} \\ G_{out\_Linear} \\ B_{out\_Linear} \end{pmatrix} = \begin{pmatrix} 3.241 & -1.537 & -0.499 \\ -0.969 & 1.876 & 0.042 \\ 0.056 & -0.204 & 1.057 \end{pmatrix} \begin{pmatrix} X_{out} \\ Y_{out} \\ Z_{out} \end{pmatrix}, \quad (4)$$

$$\begin{pmatrix} R_{out} \\ G_{out} \\ B_{out} \end{pmatrix} = \begin{pmatrix} R_{out\_Linear}^{0.45} \\ G_{out\_Linear}^{0.45} \\ B_{out\_Linear}^{0.45} \end{pmatrix}$$

Lastly, in step S1011, the display image generation unit 214 generates a display image of the proofed image held in the proofed image holding unit 213, in accordance with an instruction for image processing such as enlargement/reduction/rotation/shift processing, which is input from the input unit 101 by the user. That is, a coordinate position ($x_{in}$, $y_{in}$, $z_{in}$) of the proofed image indicated as the position of the virtual print product 403 in the virtual environment information obtained by the virtual environment information obtaining unit 211 is converted into a coordinate position ($x_{out}$, $y_{out}$, $z_{out}$) for drawing corresponding to a user instruction, and the process ends.

Representative Color Capture Intensity Map Calculation Processing (S1003)

Figure 9:
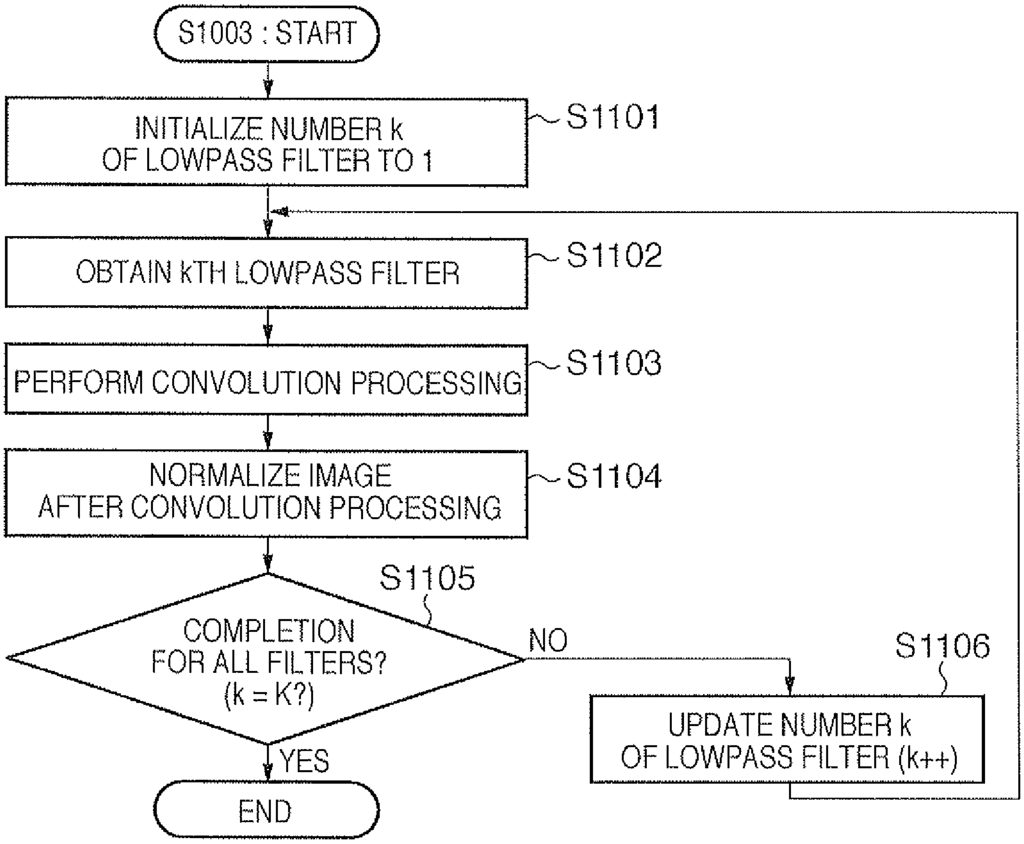
FIG. 9 is a flowchart showing representative color capture intensity map calculation processing in the first embodiment.

Representative color capture intensity map calculation processing in step S1003 will be described below with reference to a flowchart shown in FIG. 9.

First, in step S1101, a variable k indicating the number of a lowpass filter (that is, the number of a representative color) is initialized to 1 in step S1101, and a kth lowpass filter $LPF_k$ is obtained in step S1102. In step S1103, a discrete convolution operation between a luminance LUM(i,j) of the virtual illumination 402 and the kth lowpass filter $LPF_k$ for the kth representative color is performed to calculate a capture intensity $lum_k(i,j)$ for this representative color. This operation is done in accordance with:

$$lum_k(i, j) = \sum_{a=-S}^{S} \sum_{b=-S}^{S} LUM(i-a, j-b) LPF_k(a, b) \quad (5)$$

$$i = 0, \ldots, M-1, j = 0, \ldots, N-1$$

where (i,j) are the position coordinates in the illumination image formed by the virtual illumination 402, and M and N are the maximum values of the position coordinates i and j, respectively.

In step S1104, the capture intensity map $lum_k$ calculated in step S1103 is normalized to calculate a representative color capture intensity map $LUM_k$ for the number k of a representative color in accordance with:

$$LUM_k(i,j) = \{lum_k(i,j)\}/\{max\_lum_k\} \quad (6)$$

where $max\_lum_k$ is the maximum value of the capture intensity map $lum_k$ for the number k of a representative color.

In step S1105, it is determined whether processing is complete for the total number of lowpass filters K. If processing is complete, that is, k=K, processing in step S1003 ends; or if k≠K, the process advances to step S1106, in which the number k of a lowpass filter is incremented, and the process returns to step S1102.

Figure 7:
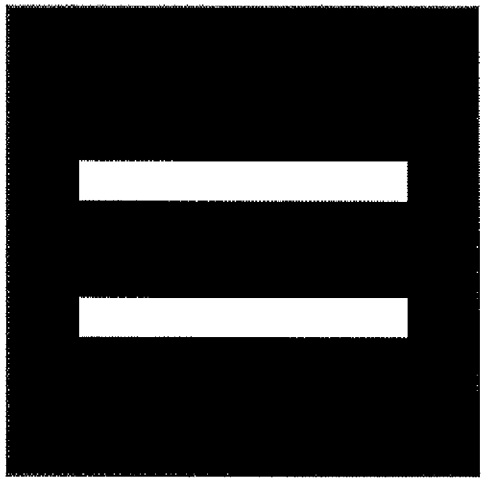
FIG. 7 is a view illustrating an example of an illumination intensity distribution in the first embodiment.
Figure 10A:
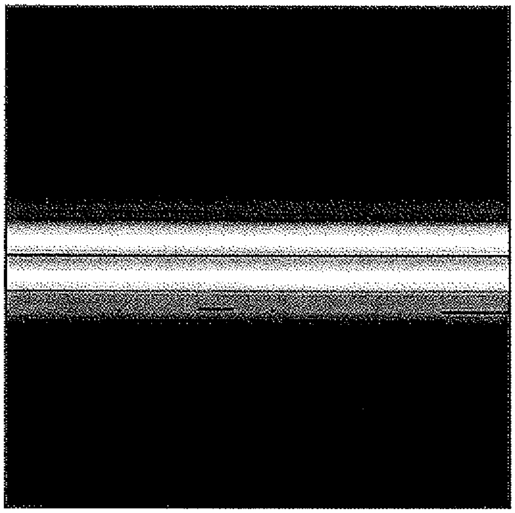
FIGS. 10A and 10B are views illustrating examples of representative color capture intensity maps in the first embodiment.
Figure 10B:
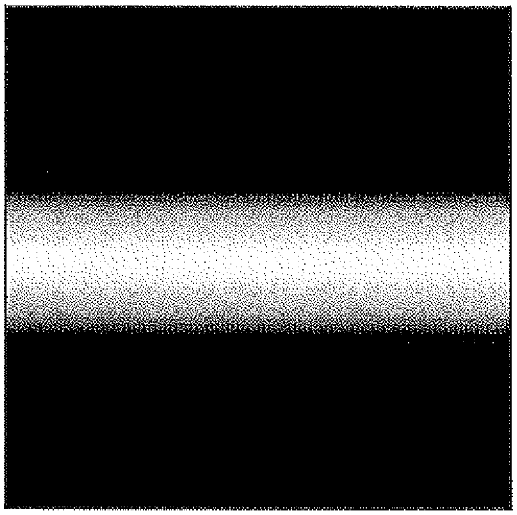

FIGS. 10A and 10B illustrate examples of representative color capture intensity maps obtained for the observation illumination image (illumination intensity distribution) shown in FIG. 7. The representative color capture intensity map is two-dimensional data obtained by holding, on a two-dimensional plane, the luminance of the observation illumination captured by each representative color, and is calculated as an observation illumination image, as shown in FIGS. 10A and 10B. FIG. 10A shows a representative color capture intensity map calculated using a lowpass filter generated for a color which captures the observation illumination the most clearly, that is, a color having a maximum image clarity evaluation value. Also, FIG. 10B shows a representative color capture intensity map calculated using a lowpass filter generated for a color which captures observation illumination the least clearly, that is, a color with a minimum image clarity evaluation value. That is, FIG. 10A shows a capture intensity map with a highest clarity, and FIG. 10B shows a capture intensity map with a lowest clarity. Note that as described above, the observation illumination image need not always be data having a value for every coordinate position in a two-dimensional plane, and its shape is not limited to a specific one as long as it is held in the illumination intensity distribution holding unit 201. A value for two-dimensional coordinates need only be held for the representative color capture intensity map as well.

Capture Intensity Calculation Processing (S1006)

Figures 11, 12:
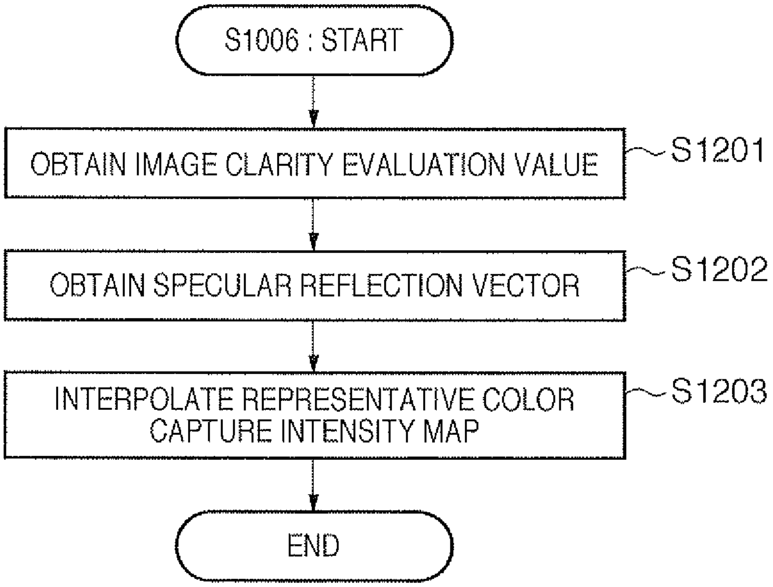
FIG. 11 is a flowchart showing capture intensity calculation processing in the first embodiment.
FIG. 12 is a table illustrating an example of an image clarity evaluation value LUT in the first embodiment.

Capture intensity calculation processing in step S1006 will be described in detail below with reference to a flowchart shown in FIG. 11.

First, in step S1201, a value indicating the full width at half maximum of the gonio-spectral reflection characteristics BRDF is obtained from the image clarity evaluation value LUT 209 as an image clarity evaluation value H corresponding to the input pixel value (RGB) of the proofing-target image. FIG. 12 illustrates an example of the image clarity evaluation value LUT 209. In the image clarity evaluation value LUT 209, a plurality of RGB values are associated with the image clarity evaluation values H, as shown in FIG. 12. Hence, to obtain a corresponding image clarity evaluation value H from the RGB value of the proofing-target pixel, the corresponding image clarity evaluation value H need only be obtained from the image clarity evaluation value LUT 209 using the RGB value as an index. Note that if the RGB value cannot be directly referred to in the image clarity evaluation value LUT 209, an image clarity evaluation value H can be obtained using an interpolation method such as tetrahedral interpolation. Note also that individual image clarity evaluation values H are measured in advance for sets of gonio-spectral reflection characteristics BRDF held in the representative color gonio-spectral reflection characteristics holding unit 204.

In step S1202, the vector R in the specular reflection direction obtained by the virtual environment information obtaining unit 211 in step S1005 is obtained.

In step S1203, a position on the representative color capture intensity map is determined using the vector R, and a corresponding representative color capture intensity map is interpolated, to calculate a capture intensity $LUM_{est}(x,y)$ of the virtual illumination 402 for a target color. This calculation is done in accordance with:

$$LUM_{est}(x, y) = \frac{H - H_{min}}{H_{max} - H_{min}} \times LUM_{max}(x, y) + \frac{H_{max} - H}{H_{max} - H_{min}} \times LUM_{min}(x, y) \quad (7)$$

where (x,y) are the coordinates of an intersection point between the specular reflection vector R at the pixel position n obtained in step S1202 and a virtual plane (observation illumination image) on which the virtual illumination 402 is set, and indicates a position on the representative color capture intensity map corresponding to the pixel position n in the proofing-target image; and $H_{max}$ and $H_{min}$ are the maximum and minimum image clarity evaluation values H, respectively, under observation illumination, which are held in the image clarity evaluation value LUT 209; and $LUM_{max}$ and $LUM_{min}$ are the representative color capture intensity maps when the image clarity evaluation value H maximizes and minimizes, respectively.

Proofing Color Calculation Processing (S1007)

Figure 13:
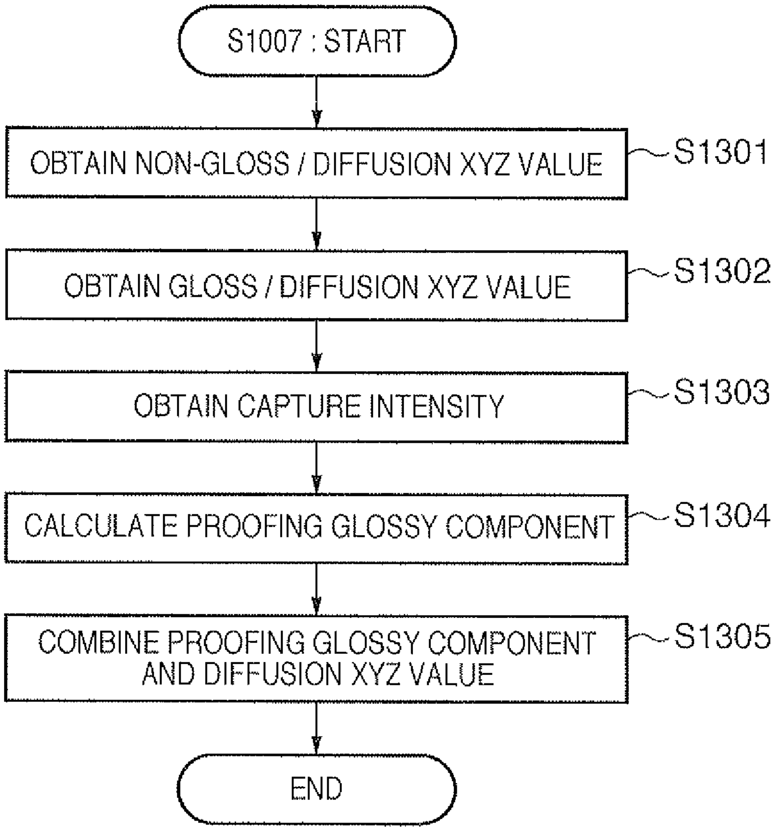
FIG. 13 is a flowchart showing proofing color calculation processing in the first embodiment.

Proofed image generation processing in step S1007 will be described in detail below with reference to a flowchart shown in FIG. 13.

First, in step S1301, a non-gloss/diffusion XYZ value corresponding to the RGB pixel value at the pixel position n in the proofing-target image is obtained from the diffusion LUT 208. In step S1302, a gloss/diffusion XYZ value corresponding to the RGB pixel value at the pixel position n in the proofing-target image is similarly obtained from the gloss LUT 207.

FIGS. 14A and 14B illustrate examples of the diffusion LUT 208 and the gloss LUT 207, respectively. As shown in FIG. 14A, the diffusion LUT 208 serves as a diffuse component holding unit which holds data measured without capturing observation illumination on, for example, an actual print product (sample print product) of a sample image having a plurality of RGB color patches. That is, diffuse reflection is measured in advance for a representative RGB value on the sample print product, and an obtained XYZ value ($X_{diff}$, $Y_{diff}$, $Z_{diff}$) is held as a diffuse component. This diffuse component is a color component of reflected light when observation illumination is not captured. Also, as shown in FIG. 14B, the gloss LUT 207 serves as a glossy component holding unit which holds data measured upon capturing observation illumination (virtual illumination 402) in the above-mentioned sample print product. That is, specular reflection of observation illumination is measured in advance for a representative RGB value on the sample print product, and an obtained XYZ value ($X_{spec}$, $Y_{spec}$, $Z_{spec}$) is held as a glossy component. The thus measured glossy component is added to the diffuse component upon capturing observation illumination. Hence, to look up the diffusion LUT 208 and gloss LUT 207 based on the input RGB pixel value of the proofing-target image, a corresponding non-gloss/diffusion XYZ value and gloss/diffusion XYZ value need only be obtained using the RGB value as an index. However, if the diffusion LUT 208 or gloss LUT 207 has no RGB value to be processed, this value may be calculated by interpolation such as tetrahedral interpolation. Any print product of an image including a plurality of colors is applicable to the above-mentioned sample print product.

In step S1303, the capture intensity $LUM_{est}(x,y)$ calculated in step S1203 is obtained. In step S1304, a proofing glossy component at each XYZ value is calculated from the non-gloss/diffusion XYZ value, the gloss/diffusion XYZ value, and the capture intensity $LUM_{est}(x,y)$, in accordance with:

$$X_{gloss}=(X_{spec}-X_{diff})\times LUM_{est}(x,y)$$

$$Y_{gloss}=(Y_{spec}-Y_{diff})\times LUM_{est}(x,y)$$

$$Z_{gloss}=(Z_{spec}-Z_{diff})\times LUM_{est}(x,y) \tag{8}$$

In step S1305, the proofing glossy component and the diffuse component are combined in accordance with:

$$X_{out}=X_{gloss}+X_{diff}$$

$$Y_{out}=Y_{gloss}+Y_{diff}$$

$$Z_{out}=Z_{gloss}+Z_{diff} \tag{9}$$

to calculate a proofing color corresponding to each pixel value in the proofing-target image, and the process ends.

According to equations (8) and (9), in this embodiment, for each pixel in the proofing-target image, a proofing glossy component is calculated by multiplying the difference between the glossy component and the diffuse component by the capture intensity, and the diffuse component is added to the proofing glossy component, to calculate a proofing color.

As described above, according to the first embodiment, first, an illumination capture intensity map for a representative color is calculated using a lowpass filter based on the gonio-spectral reflection characteristics of the representative color. The representative color capture intensity map is interpolated in accordance with the specular reflection vector for a virtual line of sight to calculate a capture intensity at each pixel position in the proofing-target image to calculate a glossy component using this capture intensity. This makes it possible to accurately reproduce color-specific glossy components.

Second Embodiment

The second embodiment according to the present invention will be described below. The system configuration of an image processing apparatus in the second embodiment is the same as in the above-mentioned first embodiment, and a description thereof will not be given. Note that especially parts different from those in the first embodiment will be described hereinafter.

Overview of Image Processing

Figure 15:
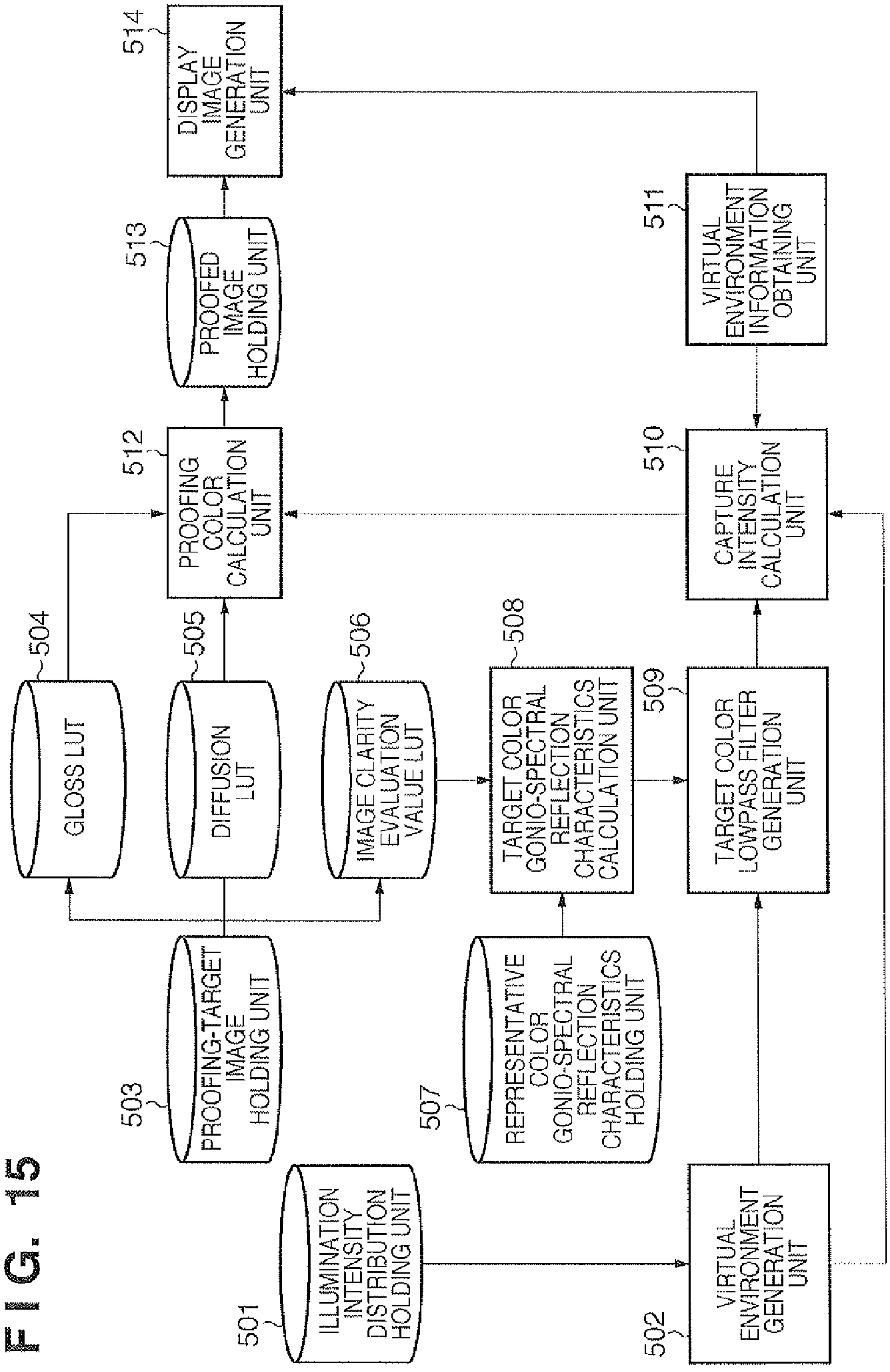
FIG. 15 is a block diagram showing a functional configuration in the second embodiment.

FIG. 15 is a block diagram showing image processing executed by the image processing apparatus in the second embodiment and the flow of data, that is, a functional configuration in this embodiment. Referring to FIG. 15, an illumination intensity distribution holding unit 501 and virtual environment generation unit 502 perform the same processing as in the illumination intensity distribution holding unit 201 and virtual environment generation unit 202, respectively, shown in FIG. 2, having been described in the above-mentioned first embodiment.

A target color gonio-spectral reflection characteristics calculation unit 508 calculates the gonio-spectral reflection characteristics of a target color using the gonio-spectral reflection characteristics of a representative color obtained from a representative color gonio-spectral reflection characteristics holding unit 507, and an image clarity evaluation value obtained from an image clarity evaluation value LUT 506. A target color lowpass filter generation unit 509 generates a lowpass filter of the target color based on virtual environment information and the gonio-spectral reflection characteristics of the target color calculated by the target color gonio-spectral reflection characteristics calculation unit 508.

A virtual environment information obtaining unit 511 obtains specular reflection vector information in the virtual line-of-sight direction, which is calculated based on virtual environment information designated via an input unit 101 by the user. A capture intensity calculation unit 510 performs filter processing for the intensity distribution (observation illumination image) of observation illumination under the virtual environment, generated by the virtual environment generation unit 502, using the target color lowpass filter and the vector information.

Note that a proofing-target image holding unit 503, gloss LUT 504, diffusion LUT 505, proofing color calculation unit 512, proofed image holding unit 513, and display image generation unit 514 perform the same processing as in the first embodiment, and a description thereof will not be given.

Details of Image Processing

Figure 16:
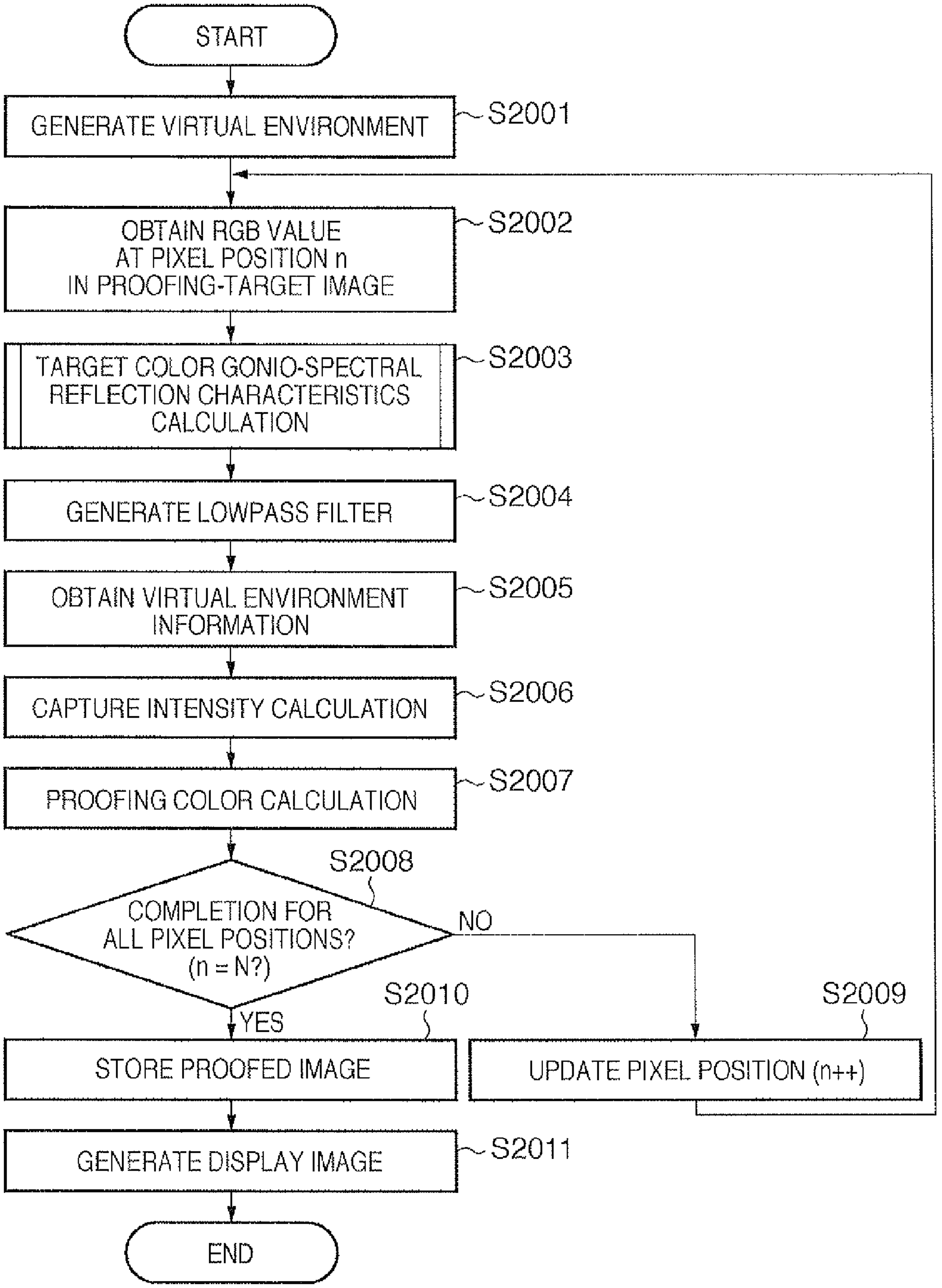
FIG. 16 is a flowchart showing image processing in the second embodiment.

Image processing in the second embodiment will be described in detail below with reference to a flowchart shown in FIG. 16.

First, in step S2001, the virtual environment generation unit 502 generates an environment, used to virtually observe a print product, by means of CG, as in the first embodiment. In step S2002, the proofing-target image holding unit 503 obtains the RGB value at a pixel position n in a proofing-target image. The RGB value at the pixel position n in the proofing-target image will be referred to as a target color hereinafter. In step S2003, the target color gonio-spectral reflection characteristics calculation unit 508 calculates gonio-spectral reflection characteristics corresponding to the target color obtained in step S2002. Processing in step S2003 will be described in more detail later.

In step S2004, the target color lowpass filter generation unit 509 generates a lowpass filter of the target color based on the gonio-spectral reflection characteristics of the target color calculated in step S2003, and the virtual environment information generated in step S2001. The lowpass filter generation method is the same as in the first embodiment; a distance Dis between virtual illumination and a virtual print product is obtained, and each emergent angle θ of gonio-spectral reflection characteristics BRDF(θ) is converted into a pixel Pix, to generate a two-dimensional low-pass filter based on the converted gonio-spectral reflection characteristics BRDF(Pix).

In step S2005, the virtual environment information obtaining unit 511 obtains position information regarding the virtual print product corresponding to the pixel position n in the proofing-target image in accordance with a user instruction, to calculate a specular reflection vector R for a line-of-sight vector E under the virtual environment, as in the first embodiment.

In step S2006, the capture intensity calculation unit 510 performs a convolution operation based on equation (5), that is, filter processing which uses the lowpass filter, as in the first embodiment, for the observation illumination image, using the coordinates of an intersection point of the specular reflection vector R and the observation illumination image as its center.

In step S2007, the proofing color calculation unit 512 calculates a proofing color for the target color calculated in step S2006, using the gloss LUT 504, the diffusion LUT 505, and the capture intensity for this target color, as in the first embodiment. In step S2008, it is determined whether proofing color calculation is complete upon processing in steps S2002 to S2007 for the total number of pixels N in the proofing-target image. If n=N, the process advances to step S2010; or if n≠N, the process advances to step S2009, in which the pixel position n is incremented, and the process returns to step S2002.

In steps S2010 and S2011, the proofing color calculation unit 512 and display image generation unit 514 generate a display image of a proofed image formed from the proofing color calculated in step S2007, for all pixels in the proofing-target image, as in the first embodiment.

Target Color Gonio-Spectral Reflection Characteristics Calculation Processing (S2003)

Figure 17:
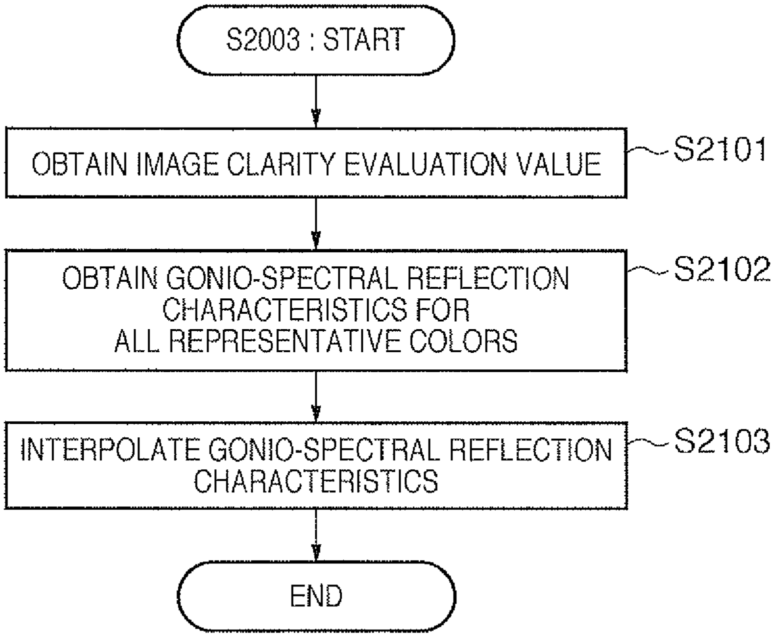
FIG. 17 is a flowchart showing target color gonio-spectral reflection characteristics obtaining processing in the second embodiment.

Target color gonio-spectral reflection characteristics calculation processing in step S2003 will be described in detail below with reference to a flowchart shown in FIG. 17.

First, in step S2101, an image clarity evaluation value H corresponding to the target color (RGB value) is obtained from the image clarity evaluation value LUT 506, as in the first embodiment. In step S2102, gonio-spectral reflection characteristics are obtained for all representative colors from the representative color gonio-spectral reflection characteristics holding unit 507. In this case, colors having the maximum and minimum image clarity evaluation values H, respectively, are used as representative colors, and gonio-spectral reflection characteristics $BRDF_{max}$ and $BRDF_{min}$ are obtained for each of these representative colors.

In step S2103, gonio-spectral reflection characteristics BRDF of the representative color are calculated in accordance with:

$$BRDF = \frac{H - H_{min}}{H_{max} - H_{min}} \times BRDF_{max} + \frac{H_{max} - H}{H_{max} - H_{min}} \times BRDF_{max} \tag{10}$$

where $H_{max}$ and $H_{min}$ are the maximum and minimum image clarity evaluation values, respectively, and the process ends.

As described above, according to the second embodiment, the gonio-spectral reflection characteristics of a target color are calculated based on the gonio-spectral reflection characteristics of a representative color, and a capture intensity on a virtual print product is calculated using a lowpass filter for the target color, which is generated based on the obtained gonio-spectral reflection characteristics. A glossy component is calculated using the obtained capture intensity for each pixel in a proofing-target image, thereby making it possible to more accurately reproduce color-specific glossy components, as in the first embodiment.

Third Embodiment

The third embodiment according to the present invention will be described below. The system configuration of an image processing apparatus in the third embodiment is the same as in the above-mentioned first embodiment, and a description thereof will not be given. Note that especially parts different from those in the first embodiment will be described hereinafter.

Overview of Image Processing

Figure 18:
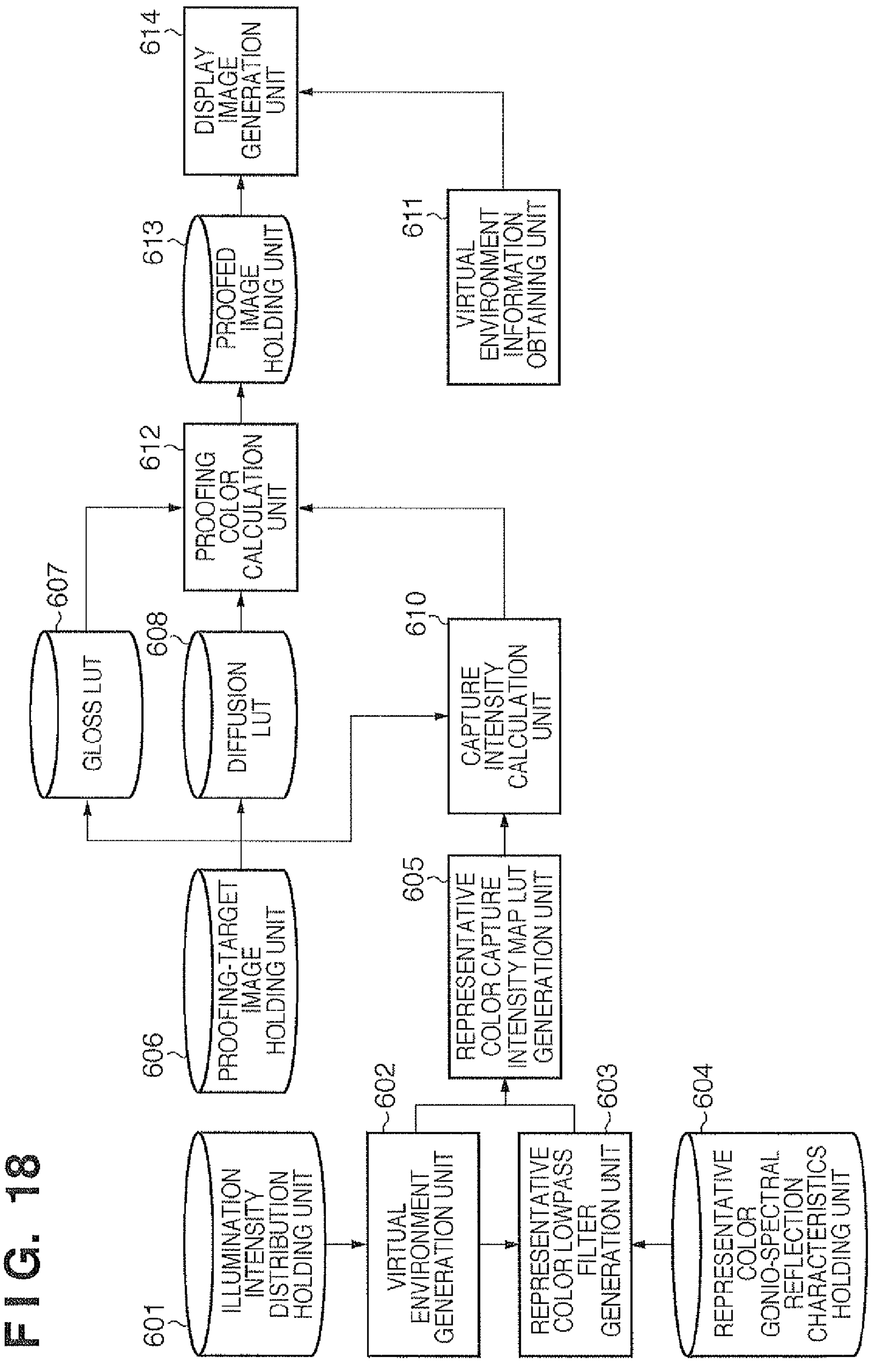
FIG. 18 is a block diagram showing a functional configuration in the third embodiment.

FIG. 18 is a block diagram showing image processing executed by the image processing apparatus in the third embodiment and the flow of data, that is, a functional configuration in this embodiment. Referring to FIG. 18, in contrast to the configuration shown in FIG. 2 in the above-mentioned first embodiment, a representative color capture intensity map LUT generation unit 605 is provided in place of the representative color capture intensity map calculation unit 205, and the image clarity evaluation value LUT 209 is omitted. Other configurations are the same as in the first embodiment, and a description thereof will not be given.

The representative color capture intensity map LUT generation unit 605 generates an LUT which associates an input pixel value and capture intensity map of a representative color with each other, using virtual illumination generated by a virtual environment generation unit 602, and a lowpass filter generated by a representative color lowpass filter generation unit 603. Although an RGB value is used as an input pixel value for a representative color in the third embodiment, the input pixel value is not limited to an RGB value as long as it indicates the representative color, and an XYZ value or an ink value may be used. A capture intensity calculation unit 610 calculates a capture intensity for a target color (RGB value) using the representative color capture intensity map LUT, and a proofing-target pixel value obtained by a proofing-target image holding unit 606.

Details of Image Processing

Figure 19:
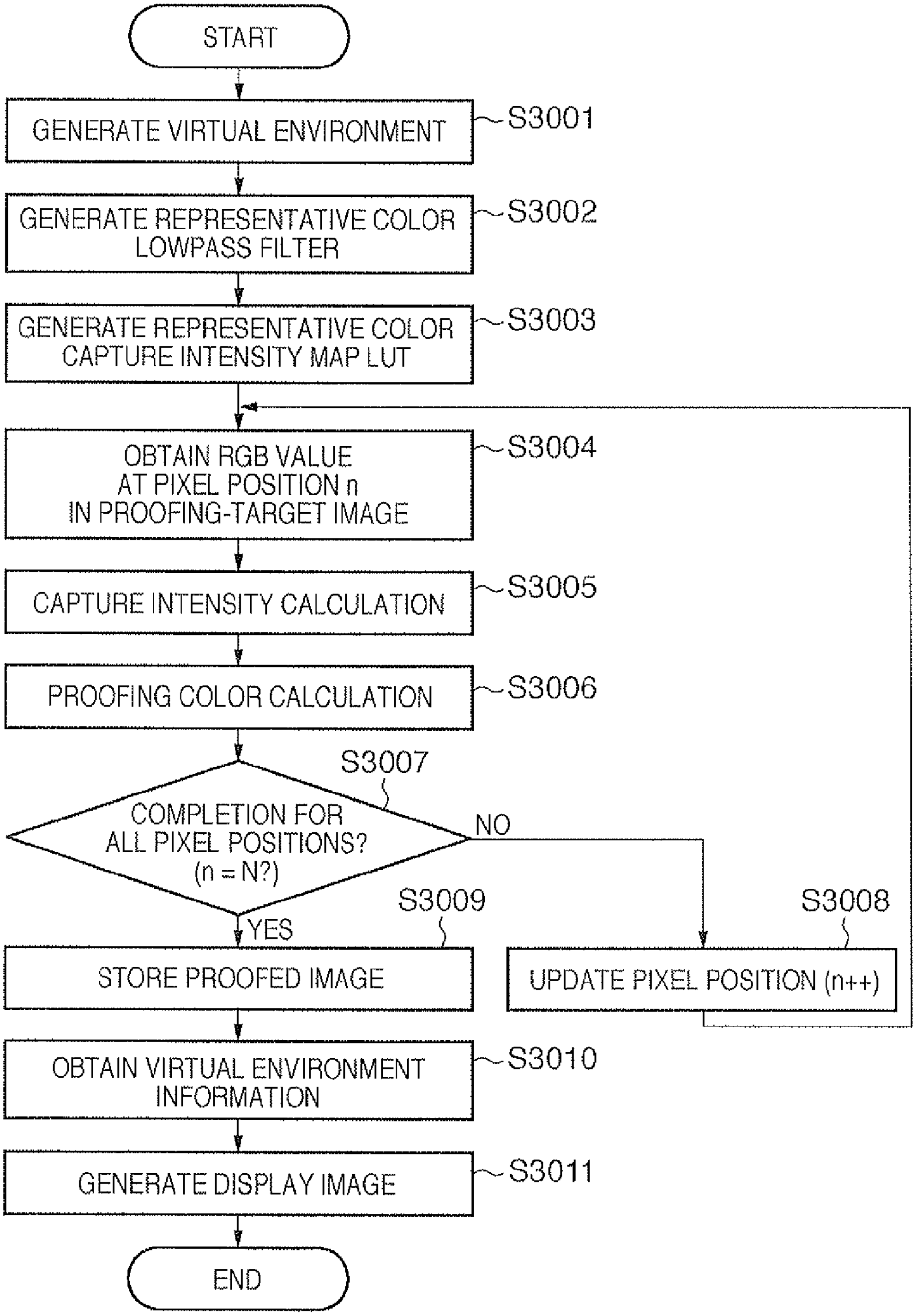
FIG. 19 is a flowchart showing image processing in the third embodiment.

Image processing in the third embodiment will be described in detail below with reference to a flowchart shown in FIG. 19.

First, in step S3001, the virtual environment generation unit 602 generates an environment, used to virtually observe a print product, by means of CG, as in the first embodiment. In step S3002, the representative color lowpass filter generation unit 603 generates a lowpass filter for a representative color, as in the first embodiment. More specifically, gonio-spectral reflection characteristics BRDF(θ) of a representative color are read from a representative color gonio-spectral reflection characteristics holding unit 604. The representative color in the third embodiment is a color obtained by dividing all color regions in a proofing-target image at a predetermined interval. Although the following description assumes 125 colors obtained by dividing each RGB value into five slices as representative colors, the number of colors is not limited to this, and 729 colors obtained by dividing each RGB value into nine slices, for example, may be used. Next, each emergent angle θ of the gonio-spectral reflection characteristics BRDF (θ) is converted into a pixel Pix for each representative color, to generate a two-dimensional lowpass filter based on the converted gonio-spectral reflection characteristics BRDF (Pix).

In step S3003, first, the representative color capture intensity map LUT generation unit 605 performs filter processing based on equation (5), as in the first embodiment, for virtual illumination 402 set in a virtual environment, for each lowpass filter of the representative color generated in step S3002. Thus, a representative color capture intensity map of each representative color is generated. Next, a table (LUT) indicating the correspondence between the RGB value and representative color capture intensity map of each color is generated. FIG. 20 illustrates an example of the representative color capture intensity map LUT generated in the third embodiment. Referring to FIG. 20, x and y are coordinates indicating the position in an illumination image formed by the virtual illumination 402, and take integers of 0 to 1024 when this illumination image has, for example, 1024×1024 pixels; and $LUM_k(x,y)$ is the capture intensity for the kth representative color at the position (x,y).

In step S3004, the proofing-target image holding unit 606 obtains the RGB value at a pixel position n in the proofing-target image. In step S3005, the capture intensity calculation unit 610 obtains a capture intensity LUM, of the virtual illumination 402 corresponding to the pixel position n in the proofing-target image and its RGB value, using the LUT generated in step S3003. Note that if the RGB value cannot be directly referred to in the representative color capture intensity map LUT, a capture intensity $LUM_{est}$ can be calculated using an interpolation method such as tetrahedral interpolation.

In step S3006, a proofing color calculation unit 612 calculates a proofing color for the RGB value, calculated in step S3005, using a gloss LUT 607, a diffusion LUT 608, and this RGB value, as in the first embodiment. In step S3007, it is determined whether proofing color calculation is complete upon processing in steps S3004 to S3006 for the total number of pixels N in the proofing-target image. If n=N, the process advances to step S3009; or if n≠N, the process advances to step S3008, in which the pixel position n is incremented, and the process returns to step S3004.

In step S3009, the proofing color calculation unit 612 stores a proofed image in a proofed image holding unit 613. In step S3010, a virtual environment information obtaining unit 611 obtains a position on the virtual print product in accordance with a user instruction, to calculate a specular reflection vector R for a line-of-sight vector E under the virtual environment, as in the first embodiment. In step S3011, a display image generation unit 614 converts the proofed image into a display image in accordance with the specular reflection vector R, as in the first embodiment, and the process ends.

As described above, according to the third embodiment, a capture intensity map for a representative color is calculated using a lowpass filter based on the gonio-spectral reflection characteristics of the representative color to generate an LUT indicating the correspondence between this map and the RGB value of the representative color. A capture intensity for each pixel position in a proofing-target image and its RGB value are calculated using this LUT to calculate a glossy component using this capture intensity, thereby making it possible to more accurately reproduce color-specific glossy components, as in the above-mentioned first embodiment.

Other Embodiments

Although an example in which two colors having the maximum and minimum image clarity evaluation values H, respectively, are used as representative colors has been given in the above-mentioned first embodiment, the representative colors are not limited to two colors as long as interpolation is performed using a plurality of representative colors. For example, it is also possible to use a maximum value $H_{max}$, minimum value $H_{min}$, and intermediate value $H_{mid}$ of an image clarity evaluation value H to perform interpolation as presented in:

When $H_{min} \le H < H_{mid}$: (11)

$$LUM_{est}(x, y) = \frac{H - H_{min}}{H_{mid} - H_{min}} \times LUM_{mid}(x, y) + \frac{H_{mid} - H}{H_{mid} - H_{min}} \times LUM_{min}(x, y)$$

When $H_{mid} \le H < H_{max}$: (12)

$$LUM_{est}(x, y) = \frac{H - H_{mid}}{H_{max} - H_{mid}} \times LUM_{max}(x, y) + \frac{H_{max} - H}{H_{max} - H_{mid}} \times LUM_{mid}(x, y)$$

Also, an example in which capture intensity for a representative color is linearly interpolated in accordance with the image clarity evaluation value when calculating a capture intensity for a target color has been given in the above-mentioned first to third embodiments. However, nonlinear interpolation such as third-order spline interpolation is also applicable in place of linear interpolation as long as interpolation is performed using a plurality of representative colors.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-179004, filed Aug. 9, 2010 which is hereby incorporated by reference herein in its entirety.

What is claimed is:

1. An image processing apparatus which performs soft proof processing of reproducing, on a monitor, a print product under observation illumination, comprising:

a characteristics holding unit configured to hold specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product;

an evaluation value holding unit configured to hold an evaluation value for each of the held color-specific gonio-spectral reflection characteristics;

an intensity distribution holding unit configured to hold an intensity distribution of the observation illumination;

a lowpass filter generation unit configured to obtain the gonio-spectral reflection characteristics for each of a plurality of representative colors from said characteristics holding unit, and to generate a lowpass filter corresponding to the gonio-spectral reflection characteristics for each of the representative colors, the representative colors corresponding to the evaluation values held in said evaluation value holding unit;

a map generation unit configured to perform filter processing on the intensity distribution of the observation illumination held in said intensity distribution holding unit, for each of the representative colors, by means of the lowpass filter corresponding to the representative color, in order to generate a map indicating a capture intensity distribution of observation illumination for the representative color;

an intensity calculation unit configured to obtain an evaluation value corresponding to a color of a pixel in a proofing-target image from said evaluation value holding unit, and to interpolate a capture intensity at a position corresponding to the pixel in the map for each of the representative colors, based on the evaluation value, in order to calculate a capture intensity of the observation illumination for the pixel, for each pixel in the proofing-target image;

a proofing color calculation unit configured to obtain the glossy component and the diffuse component corresponding to a color of a pixel in the proofing-target image from said characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

2. The apparatus according to claim 1, further comprising:

a virtual environment generation unit configured to generate a virtual environment, used to observe a print product of the proofing-target image, in accordance with the intensity distribution of the observation illumination held in said intensity distribution holding unit; and an obtaining unit configured to obtain a specular reflection vector for a line-of-sight vector under the virtual environment, for each pixel in the proofing-target image, wherein said intensity calculation unit determines a position corresponding to a pixel in the proofing-target image in the map for each of the representative colors, based on the specular reflection vector.

3. The apparatus according to claim 1, wherein the evaluation value includes a full width at half maximum of the gonio-spectral reflection characteristics function which indicates a variance of the gonio-spectral reflection characteristics.

4. An image processing apparatus which generates a proofed image used to reproduce, on a monitor, a print product under observation illumination, comprising:

a characteristics holding unit configured to hold specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product;

an evaluation value holding unit configured to hold an evaluation value for each of the held color-specific gonio-spectral reflection characteristics;

an intensity distribution holding unit configured to hold an intensity distribution of the observation illumination;

a characteristics calculation unit configured to obtain the gonio-spectral reflection characteristics for each of a plurality of representative colors from said gloss characteristics holding unit, and to calculate gonio-spectral reflection characteristics for a color of each pixel in the proofing-target image by means of obtaining the evaluation value corresponding to the color of the pixel from said evaluation value holding unit, and interpolating the gonio-spectral reflection characteristics for each of the representative colors, based on the evaluation value, the representative colors corresponding to the evaluation values held in said evaluation value holding unit a lowpass filter generation unit configured to generate a lowpass filter corresponding to the gonio-spectral reflection characteristics for a color of each pixel in the proofing-target image;

an intensity calculation unit configured to perform filter processing on the intensity distribution of the observation illumination held in said illumination intensity distribution holding unit, by means of the lowpass filter corresponding to a color of a pixel in the proofing-target image, in order to calculate a capture intensity distribution of the observation illumination for the pixel, for each pixel in the proofing-target image;

a proofing color calculation unit configured to obtain the glossy component and the diffuse component corresponding to a color of a pixel in the proofing-target image from said characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

5. The apparatus according to claim 4, further comprising:

a virtual environment generation unit configured to generate a virtual environment, used to observe a print product of the proofing-target image, in accordance with the intensity distribution of the observation illumination held in said intensity distribution holding unit; and an obtaining unit configured to obtain a specular reflection vector for a line-of-sight vector under the virtual environment, for each pixel in the proofing-target image, wherein said intensity calculation unit determines a position, in the intensity distribution of the observation illumination held in said intensity distribution holding unit, corresponding to a pixel in the proofing-target image, based on the specular reflection vector.

6. The apparatus according to claim 4, wherein the evaluation value includes a full width at half maximum of the gonio-spectral reflection characteristics function which indicates a variance of the gonio-spectral reflection characteristics.

7. An image processing apparatus which generates a proofed image used to reproduce, on a monitor, a print product under observation illumination, comprising:

a characteristics holding unit configured to hold specular reflection of the observation illumination at a sample print product having a plurality of colors printed thereon as color-specific glossy components, diffuse reflection of the observation illumination at the sample print product as color-specific diffuse components, and color-specific gonio-spectral reflection characteristics at the sample print product;

an intensity distribution holding unit configured to hold an intensity distribution of the observation illumination;

a lowpass filter generation unit configured to obtain the gonio-spectral reflection characteristics for each of a plurality of representative colors from said gloss characteristics holding unit, and to generate a lowpass filter corresponding to the gonio-spectral reflection characteristics, where the representative colors include a plurality of colors in a color region of a proofing-target image;

a map generation unit configured to perform filter processing on the intensity distribution of the observation illumination held in said intensity distribution holding unit by means of the lowpass filter, in order to generate a map indicating a capture intensity distribution of observation illumination for the representative color, and to generate a table indicating a relationship between the representative color and the map, for each of the representative colors;

an intensity calculation unit configured to calculate a capture intensity of the observation illumination corresponding to a position and a color of a pixel in the proofing-target image by accessing up the table, for each pixel in the proofing-target image;

a proofing color calculation unit configured to obtain the glossy component and the diffuse component corresponding to a color of a pixel in the proofing-target image from said characteristics holding unit, to multiply the difference between the glossy component and the diffuse component by the capture intensity to calculate a proofing glossy component, and to add the diffuse component to the proofing glossy component in order to calculate a proofing color of the pixel, for each pixel in the proofing-target image; and a display image generation unit configured to convert the proofing color into a signal value for the monitor to generate a display image, for each pixel in the proofing-target image.

8. An image processing method for an image processing apparatus comprising a characteristics holding unit, an evaluation value holding unit, a lowpass filter generation unit, a map generation unit, an intensity calculation unit, a proofing color calculation unit, and a display image generation unit, wherein the image processing apparatus performs soft proof processing of reproducing, on a monitor, a print product under observation illumination, wherein:

said characteristics holding unit is configured to hold specular reflection of the observation illumination as color-specific glossy components, diffuse reflection of the observation illumination as color-specific diffuse components, and color-specific gonio-spectral reflection characteristics;

said evaluation value holding unit is configured to hold an evaluation value for each of the held color-specific gonio-spectral reflection characteristics; and said intensity distribution holding unit is configured to hold an intensity distribution of the observation illumination;

said method comprising:

a lowpass filter generation step of obtaining the gonio-spectral reflection characteristics for each of a plurality of representative colors from said characteristics holding unit, and generating a lowpass filter corresponding to the gonio-spectral reflection characteristics for each of the representative colors, the representative colors corresponding to the evaluation values held in said evaluation value holding unit;

a map generation step of performing filter processing on the intensity distribution of the observation illumination held in said intensity distribution holding unit, for each of the representative colors, by means of the lowpass filter corresponding to the representative color, in order to generate a map indicating a capture intensity distribution of observation illumination for the representative color;

an intensity calculation step of obtaining an evaluation value corresponding to a color of a pixel in a proofing-target image from said evaluation value holding unit, and interpolating a capture intensity at a position corresponding to the pixel in the map for each of the representative colors, based on the evaluation value, in order to calculate a capture intensity of the observation illumination for the pixel, for each pixel in the proofing-target image;

a proofing color calculation step of obtaining the glossy component and the diffuse component corresponding to a color of a pixel in the proofing-target image from said characteristics holding unit, multiplying the difference between the glossy component and the diffuse component by the capture intensity to calculate a proofing glossy component, and adding the diffuse component to the proofing glossy component in order to calculate a proofing color of the pixel, for each pixel in the proofing-target image; and a display image generation step of converting the proofing color into a signal value for the monitor to generate a display image, for each pixel in the proofing-target image.

9. A non-transitory computer-readable storage medium storing a program for causing a computer to function as each unit of an image processing apparatus defined in claim 1 by executing the program by the computer.

* * * * *